(12) United States Patent
Carrel et al.

(10) Patent No.: US 11,524,123 B2
(45) Date of Patent: Dec. 13, 2022

(54) SAFETY ASSEMBLY AND MEDICAL DEVICE WITH SAFETY ASSEMBLY

(71) Applicant: Becton Dickinson France, Le Pont de Claix (FR)

(72) Inventors: Franck Carrel, Le Pont de Claix (FR); Lionel Maritan, Le Pont de Claix (FR); Freddy Mills, Le Pont de Claix (FR)

(73) Assignee: Becton Dickinson France, Le Pont de Claix (FR)

( * ) Notice: Subject to any disclaimer, the term of this patent is extended or adjusted under 35 U.S.C. 154(b) by 337 days.

(21) Appl. No.: 16/647,162

(22) PCT Filed: Sep. 13, 2018

(86) PCT No.: PCT/EP2018/074717
§ 371 (c)(1),
(2) Date: Mar. 13, 2020

(87) PCT Pub. No.: WO2019/053111
PCT Pub. Date: Mar. 21, 2019

(65) Prior Publication Data
US 2020/0222637 A1    Jul. 16, 2020

(30) Foreign Application Priority Data
Sep. 14, 2017 (EP) .................................... 17306185

(51) Int. Cl.
*A61M 5/32* (2006.01)
*A61M 5/34* (2006.01)

(52) U.S. Cl.
CPC ........ *A61M 5/3202* (2013.01); *A61M 5/3216* (2013.01); *A61M 5/345* (2013.01)

(58) Field of Classification Search
CPC . A61M 5/3202; A61M 5/3213; A61M 5/3216
See application file for complete search history.

(56) References Cited

U.S. PATENT DOCUMENTS 5,879,345 A * 3/1999 Aneas ................... B65D 51/002
                                                    215/277
6,695,819 B2 * 2/2004 Kobayashi .......... A61M 5/3216
                                                    604/263

(Continued)

FOREIGN PATENT DOCUMENTS

CN         1196023 A      10/1998
CN         1741829 A       3/2006
(Continued)

*Primary Examiner* — Laura A Bouchelle
(74) *Attorney, Agent, or Firm* — The Webb Law Firm

(57) ABSTRACT

The invention relates to a safety assembly having—an attachment ring attached to the tip of the container and—a safety device covering at least the distal end of the needle, the safety device attached to the attachment ring. The attachment ring has an inner ring having an inner face provided with a snap feature, which engages a complementary snap feature on the tip of the container to prevent axial movement of the inner ring with respect to the container. The snap feature moves radially to engage the complementary snap feature on the tip of the container; and an outer ring is fixed on the inner ring, with a sleeve portion surrounding at least a portion of the inner ring to prevent radial movement of the snap feature once the snap feature has engaged the complementary snap feature on the tip of the container.

16 Claims, 14 Drawing Sheets

(56) References Cited

U.S. PATENT DOCUMENTS

| | | | |
|---|---|---|---|
| 7,331,941 B2 | 2/2008 | Vetter et al. | |
| 9,839,752 B2 | 12/2017 | Fournier et al. | |
| 2003/0088215 A1 | 5/2003 | Ferguson et al. | |
| 2015/0313525 A1* | 11/2015 | Ebetsberger | A61B 5/150389 600/576 |
| 2017/0258990 A1* | 9/2017 | Wei | A61M 5/3216 |

FOREIGN PATENT DOCUMENTS

| | | |
|---|---|---|
| EP | 1466638 A2 | 10/2004 |
| EP | 1466638 A3 | 5/2006 |
| WO | 2004/071560 A1 | 8/2004 |
| WO | 2014/131981 A1 | 9/2014 |
| WO | 2016/198387 A1 | 12/2016 |

\* cited by examiner

SAFETY ASSEMBLY AND MEDICAL DEVICE WITH SAFETY ASSEMBLY

CROSS-REFERENCE TO RELATED APPLICATIONS

This application is the United States national phase of International Application No. PCT/EP2018/074717 filed Sep. 13, 2018, and claims priority to European Patent Application No. 17306185.4 filed Sep. 14, 2017, the disclosures of which are hereby incorporated by reference in their entirety.

BACKGROUND OF THE INVENTION

Field of the Invention

The present invention relates to a safety assembly for preventing needle stick injury with a needle of a medical device, and also to a medical device provided with such a safety assembly.

Description of Related Art

Medical devices provided with sharp pointed needles are of daily practice among the medical community in order to perform injections into or to take samples from tissues, veins or arteries of the patient. Medical devices having needles may comprise, but not be limited to, injection devices such as syringes, pen-injectors, catheters or blood collection devices. Sharp pointed needles of these medical devices present an inherent risk of needle stick injury to the medical staff and/or the patients and are thus usually covered by a protective cap before use. This cap can preserve the needle not only from contamination but also from undesired contacts or punctures that could occur during transport and delivery of the medical devices. Obviously, such a cap needs to be removed immediately before use of the medical device. Also, the needle needs to be protected after use of the medical device in order to prevent accidental needle sticks.

WO 2016/198387 A1 discloses a safety device which comprises a protective cap and a shield to be mounted on a tip of a syringe. The safety device is attached to the syringe tip by means of a mounting ring which is to be clipped on a bump formed on the syringe tip.

However, the proposed structure is relatively weak against axial force that may be applied to the safety assembly and under some circumstance the ring may be easily pulled out from the syringe tip.

Also, the medical device is typically sterilized only after the mounting ring is assembled with the syringe, and as a result the reliability of clipping between the syringe tip and the mounting ring is limited.

SUMMARY OF THE INVENTION

In view of the above, an object of the present invention is to improve reliability of the connection between a safety device and a medical container, thereby reducing a risk of the safety device being pulled out and unintentional exposure of a needle of the medical device.

A first aspect of the invention concerns a safety assembly for preventing needle stick injury with a needle, the needle having a proximal end fixed to a tip of a medical container and a pointed distal end, the safety assembly comprising:
an attachment ring configured to be attached to the tip of the container;
a safety device configured to cover at least the distal end of the needle, the safety device being attached to the attachment ring;
the attachment ring comprising:
an inner ring having an inner face provided with a snap feature, the snap feature being configured to engage a complementary snap feature on the tip of the container in order to prevent axial movement of the inner ring with respect to the container, the snap feature being configured to move radially to engage the complementary snap feature on the tip of the container;
an outer ring fixed on the inner ring, the outer ring comprising a sleeve portion configured to surround at least a portion of the inner ring in order to prevent radial movement of the snap feature once the snap feature has engaged the complementary snap feature on the tip of the container.

The sleeve portion of the outer ring prevents radial movement of the snap feature of the inner ring. Since the radial movement of the snap feature is required to detach the inner ring from the tip of the medical container, this configuration prevents the inner ring from being pulled out of the container tip by accident. This configuration increases reliability of the connection between the medical container and the attachment ring, and then between the medical container and the safety assembly. As a matter of fact, the outer ring and the inner ring may be chosen to have the same thermal expansion, and consequently, the outer ring enables to maintain the inner ring on the container's tip, even after the sterilization process.

According to one embodiment, the inner ring comprises a distal ring and one mounting finger extending proximally from the distal ring, the snap feature being formed at a proximal end of said mounting finger, the mounting finger being able to be deformed radially outwardly, the outer ring being fixed on the inner ring such that the sleeve portion surrounds the at least one mounting finger to prevent radial deformation of the at least one mounting finger. The inner ring is configured to be inserted axially on the container's tip. During axial insertion of the inner ring on the tip of the container, the mounting fingers are flexed outwardly so that the snap feature may engage the complementary snap feature of the container. Once the snap feature engages the complementary snap feature of the container, the inner ring is maintained in this position by the outer ring which prevents radial deformation of the mounting fingers. More precisely, the sleeve portion prevents the mounting fingers to be flexed outwardly and consequently they prevent radial movement of the snap feature. As long as the snap feature cannot move radially, they cannot disengage the complementary snap feature, such that the attachment ring cannot move axially. The inner ring is then maintained snapped on the container's tip by the outer ring. The attachment ring enables then a more secure attachment between the safety device and the container.

According to another embodiment, the inner ring comprises two half rings having each an inner face provided with at least a snap feature, the two half rings being configured to be interlocked around the tip of the container such that the snap features engage complementary snap features on the tip of the container in order to prevent axial movement of the inner ring with respect to the container, the sleeve portion of the outer ring being configured to surround the two half rings to prevent radial movement of the two half rings.

According to this embodiment, the two half rings are assembled around the container's tip and then maintained together by the outer ring. The snap features are maintained engaged with the complementary snap feature as long as they cannot move radially, such that the safety device cannot be pulled out from the container's tip.

Advantageously, the two half rings may be identical, each half ring comprising first and second hook portions arranged such that the first and second hook portions of one half ring respectively engage the second and first hook portions of the other half ring. According to this embodiment, since the two half rings have the identical design, the cost for producing the half rings and therefore the safety assembly can be reduced. The half rings have hook portions for engaging with each other and no additional fixing means will be required. This can further reduce the cost for producing the safety assembly.

Advantageously, the two half rings may be connected by a hinge. According to this embodiment, the two half rings are configured to pivot around the hinge. According to this embodiment, the two half rings can pivot around the hinge between an engaged position in which the half rings are engaged with each other and a disengaged position in which the half rings are disengaged from each other. This can facilitate the process for assembling the inner ring with the medical container.

Advantageously, the outer ring is snapped on the inner ring.

More precisely, the outer ring preferably comprises at least a clipping feature clipped into a complementary clipping feature of the inner ring. This embodiment provides an easy and secure way to maintain the outer ring around the inner ring.

According to one embodiment, the inner ring may have a flange extending radially outwardly, and the outer ring may have at least one locking finger extending proximally and having a proximal end extending radially inwardly, the proximal end of the at least one locking finger being engaged with the flange of the inner ring to interlock the outer ring with the inner ring. According to this embodiment, the locking finger(s) of the outer ring engage(s) with the flange of the inner ring. It is ensured that the outer ring cannot be pulled out from the inner ring.

According to different embodiments:
the flange may extend from a proximal end of the inner ring, or
the flange may be arranged on a circumferential outer face of the inner ring.

Advantageously, the flange of the inner ring may comprise a proximal wall inclined relative to a plane which extends perpendicular to a central axis of the inner ring, in order to ease manufacturing of the inner ring.

According to this embodiment, the flange of the inner ring is delimited by an inclined wall. This increases pull-out force required to pull the outer ring from the inner ring and ensures that the attachment ring cannot be removed easily by accident.

According to one embodiment, the outer ring has an inner protrusion extending radially inwardly and being configured to frictionally engage the tip of the container. According to this embodiment, the inner protrusion of the outer ring is frictionally engaged with the tip of the container when the safety assembly is attached to the medical container. Therefore, rotational torque which may be applied on the outer ring is prevented from being transmitted to the inner ring.

Advantageously, the inner ring and the outer ring are made of a material having the same thermal expansion. It enables a better attachment of the attachment ring to the container's tip after sterilization process.

Advantageously, the inner ring and the outer ring are made of plastic.

According to a preferred embodiment, the safety device comprises:
a protective cap configured to cover the needle and inserted on the attachment ring and
a protective arm attached to the attachment ring by a pivot link, the protective arm being pivotally movable between a storage position in which the protective arm is interlocked with the protective cap, a retracted position in which the protective arm releases the protective cap to give access to the needle, and a safety position in which the protective arm covers the needle, Advantageously, the protective cap is configured to be removed from the tip of the container by axial movement in a distal direction.

Advantageously, the protective arm comprises a proximal extremity provided with a cam surface, the protective cap comprising a proximal extremity provided with an engaging peg, the cam surface and the engaging peg being arranged so that, when the safety assembly is mounted around the tip of the container, removing the protective cap from the tip by a distal movement displaces the protective arm from the storage position to the retracted position.

A second aspect of the invention concerns a medical device comprising:
a medical container having a barrel, a tip extending from the barrel in a distal direction, and a complementary snap feature on the tip;
a needle attached to the tip of the medical container; and
the safety assembly according to the first aspect of the invention, the safety assembly being attached to the tip of the medical container such that the snap feature of the inner ring is engaged with the complementary snap feature of the medical container.

According to one embodiment, the complementary snap feature may be a bump, the snap feature comprising a groove delimited proximally by an inwardly protruding protrusion configured to be inserted proximally from the bump.

According to another embodiment, the complementary snap feature may be a groove, the snap feature comprising an inwardly protruding protrusion configured to be inserted into the groove.

Advantageously, the container is made of glass.

BRIEF DESCRIPTION OF THE DRAWINGS

Embodiments of the present invention will be hereinafter described by way of example, with reference to the accompanying figures, in which.

DESCRIPTION OF THE INVENTION

In this application, the distal end of a component or apparatus should be understood as meaning the end farthest from the hand of the user and the proximal end must be understood as meaning the end closest to the hand of the user. As such, the distal direction should be understood as the direction farther away from the hand of the user, and the proximal direction is the opposite direction, i.e., the direction towards the hand of the user. The proximal and distal directions are in parallel to the direction in which a needle of a medical container is to extend. The radial direction should be understood as the direction perpendicular to the proximal and distal directions.

Figure 1:
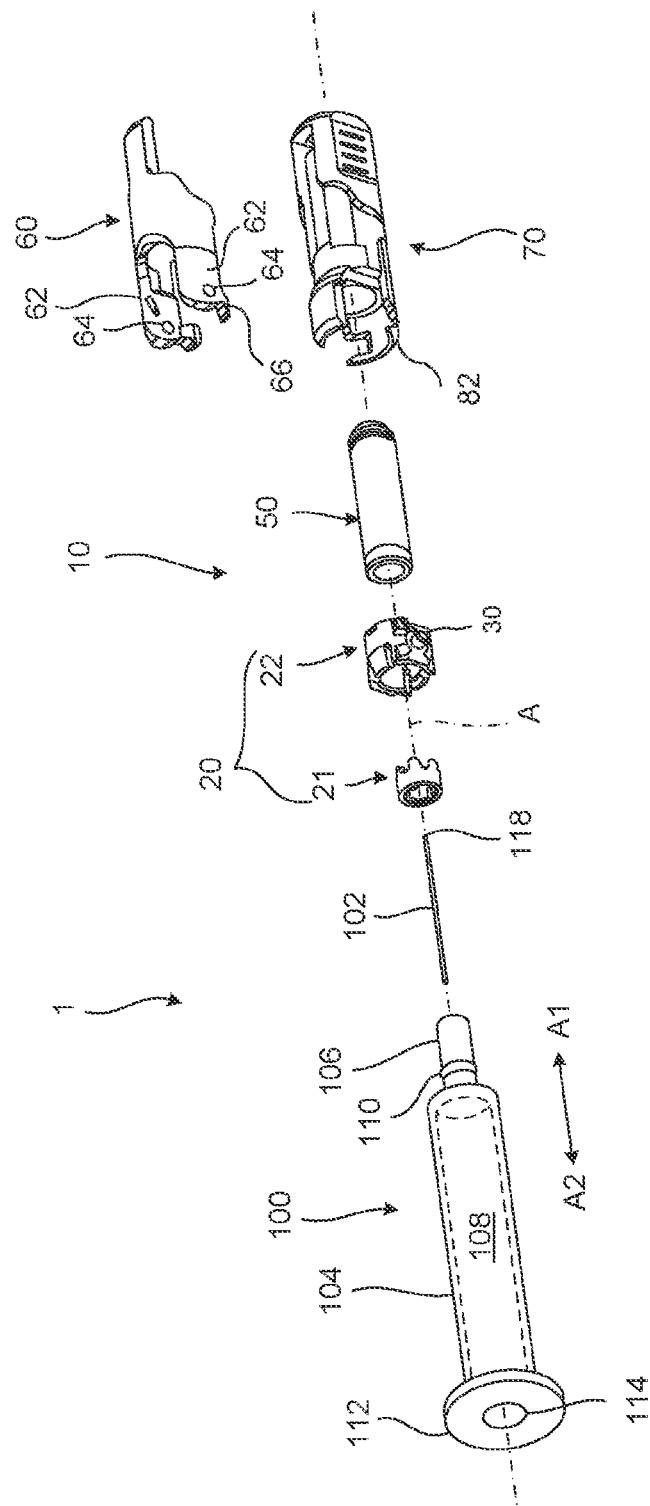
FIG. 1 is an exploded perspective view illustrating a medical device according to one example.

FIG. 1 shows an exploded perspective view illustrating a medical device 1 according to one example. The medical device 1 generally has an elongated shape extending along an axial line A, which may also be referred to as "central axis" in this application.

The medical device 1 comprises a medical container 100 having an elongated barrel 104 and a longitudinal tip 106 extending distally (as indicated by arrow A1) from a distal end of the barrel 104, and a needle 102 attached to the tip 106 of the container 100.

The barrel 104 has a tubular shape and defines a reservoir 108 inside thereof for containing a medical solution. The barrel 104 has a flange 112 extending radially outwardly from the proximal end of the barrel 104. The barrel 104 has a circular opening 114 which is generally concentric with the barrel 104 and in fluid communication with the reservoir 108. The opening 114 allows a plunger (not shown) to advance within the reservoir 108 in the distal direction through the opening 114 to eject the medical solution contained in the reservoir 108. The medical solution which is to be contained in the reservoir 108 may comprise, but not be limited to pharmaceutical composition, vitamins, a vaccine or the like.

The container tip 106 is a generally tubular element having a smaller diameter than the barrel 104. The tip 106 is smoothly connected to the distal end of the barrel 104. The barrel 104 and the tip 106 are preferably made of glass and integrally formed with each other.

Figure 5:
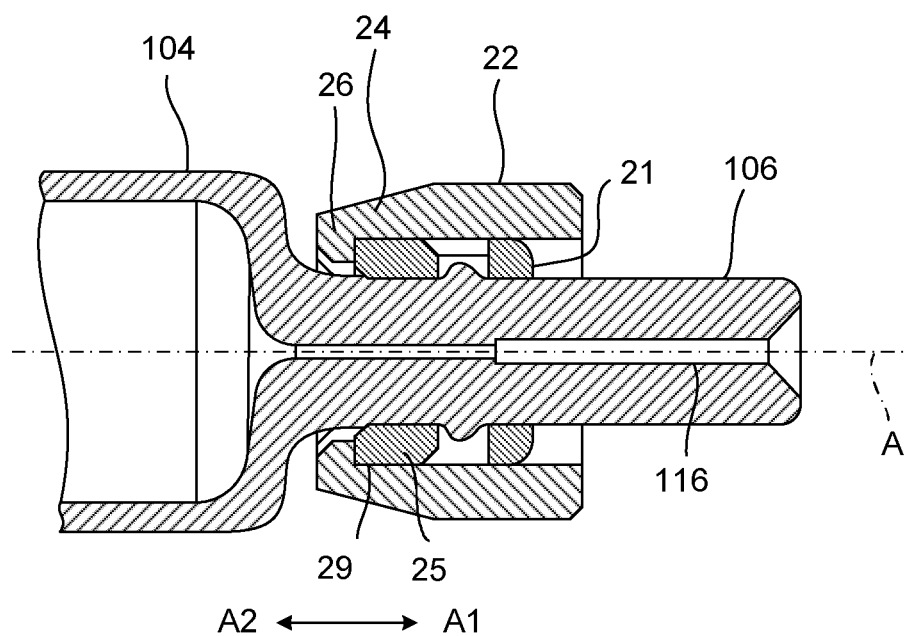
FIG. 5 is a longitudinal sectional view illustrating the tip of the container provided with the attachment ring.

The tip 106 defines an inner channel 116 extending through the tip 106 between its proximal and distal ends (see also FIG. 5). The inner channel 116 is in fluid communication with the reservoir 108.

The tip of the container 100 has a complementary snap feature 110. In this example, the complementary snap feature 110 is a bump on an outer circumferential face of the tip 106. The bump 110 protrudes radially outwardly relative to the remaining surface of the tip 106. However, the complementary snap feature 110 could also be a groove.

The needle 102 has a pointed distal end 118 and a proximal end 120 which is fixed within the inner channel 116 of the tip 106 by glue or any other known means acceptable to medical use. The needle 102 is a hollow element the inside of which is in fluid communication with the reservoir 108 through the inner channel 116 of the tip 106. When the needle 102 is assembled with the container 100, the distal end 108 of the needle 102 sticks out of the tip 106.

The medical device 1 is provided with a safety assembly 10 for preventing needle stick injury with the needle 102.

The safety assembly 10 comprises an attachment ring 20, and a safety device attached to the attachment ring and intended to cover at least the pointed distal end of the needle.

The attachment ring 20 comprises an inner ring 21 and an outer ring 22.

The inner ring 21 is configured to be clipped on the tip of the container. More precisely, the inner ring 21 is provided with at least a snap feature configured to engage the complementary snap feature of the tip 106 of the container.

The inner ring 21 and the outer ring 22 are preferably made of a plastic suitable to medical use. The inner ring 21 and the outer ring 22 may be made of the same material or of different materials. The material used for the inner ring 21 and the outer ring 22 may comprise, but not be limited to, high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and their combinations. Using such plastic materials, the inner and outer rings can be provided with suitable shapes (e.g. self-engaging features, sharp edges, etc.) that allow snapping the outer ring to the inner ring with a high pullout resistance.

Besides, as compared to a snapped connection between a glass tip comprising a bump protruding radially outwardly and a conventional plastic ring comprising a complementary groove engaging the bump, the snapped connection between the inner and outer rings has a greater pullout resistance. Indeed, glass forming does not allow creating a bump with sharp edges, which is detrimental to the pullout force of the snapped connection with a conventional plastic ring. This problem is avoided by providing a connection (between the tip and the attachment ring) whose pull-out resistance essentially depends on the strong snapped connection between the inner ring and outer ring that are both made of plastic, rather than on the weaker connection between the glass tip and the plastic ring. As a result, the pullout resistance of the connection between the safety device and the glass tip can be increased.

In the illustrated examples, wherein the complementary snap feature is a bump protruding radially outwardly from an outer face of the tip of the container, the snap feature comprises a groove delimited proximally by an inwardly protruding protrusion 25a. The groove is configured to receive the bump. Conversely, the complementary snap feature could be a groove and the snap feature could be a lip configured to be inserted into the groove.

By "safety device" is meant in the present text a device configured to protect a user from needle stick injury after the injection of the medical solution has been carried out.

According to an embodiment, the safety device comprises a protective arm 60 adapted to be attached to the attachment ring 20, and a protective cap 70 adapted to be inserted on the attachment ring. The protective cap and the protective arm are preferably similar to those described in the patent application WO2016/198387.

More precisely, the protective cap 70 is adapted to be mounted on the tip of the medical container to cover the needle. The protective cap 70 comprises a proximal extremity provided with at least an engaging peg 82. The protective cap 70 may comprise a needle shield 50 and a rigid shield 80 or only one single shield. The protective cap 70 preferably comprises a sleeve portion configured to be inserted onto the attachment ring 20.

The protective arm 60 is attached to the attachment ring 20 by a pivot link such that it may adopt:
 a storage position where it is interlocked with the protective cap;
 a retracted position where it gives access to the needle and
 a safety position where it covers the needle.

The protective arm 60 comprises a cam surface 66 at its proximal extremity. The cam surface 66 of the protective arm and the engaging peg 82 of the protective cap are configured so that, removing the protective cap by axial movement shifts the protective arm from a storage position to a retracted position.

The outer ring 22 comprises fixing means configured to pivotally fix the protective arm 60 on the outer ring 22. The fixing means may for example comprise inserts 30 (only one of them is visible in FIG. 1) sticking out radially outwardly from the outer ring, while the protective arm comprises openings 64 configured to receive the inserts 30 so that the protective arm may rotate with respect to the outer ring.

The protective arm 60 has a distal cover 68 and two legs 62 extending from the distal cover 68 in the proximal direction A2. Although not illustrated in the drawings, the distal cover 68 may comprise a notch intended to accommodate the distal end 118 of the needle 102.

The protective arm 60 and the rigid shield 80 may be made of plastic.

The needle shield 50 is a tubular element defining an inner cavity for accommodating the needle 102. The needle shield 50 is made of elastomeric material and dimensioned to be accommodated by the rigid shield 80.

Figure 15A:
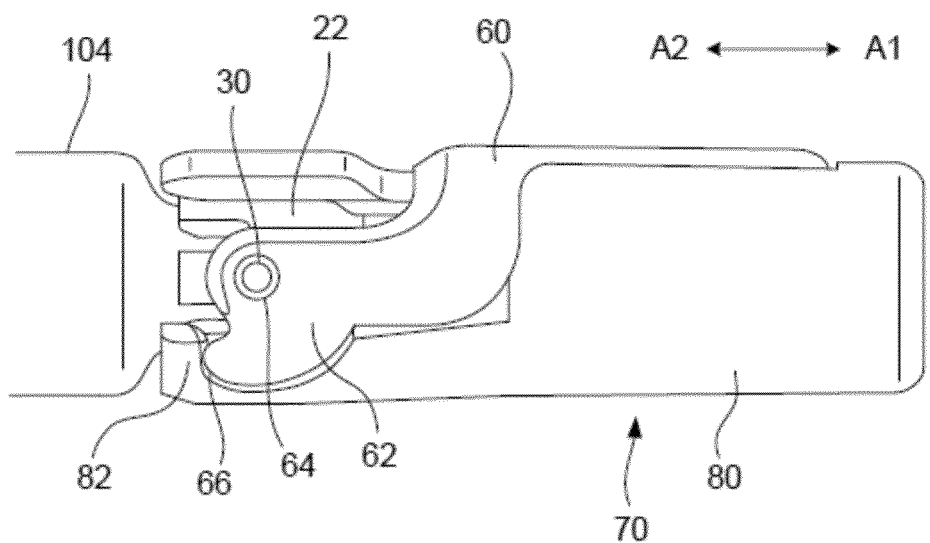
FIGS. 15A to 15D show the process for using the medical device according to one example.

FIG. 15A shows the protective arm 60 in a storage position. In this position, the protective arm 60 is interlocked with the protective cap 70, which covers the distal end 118 of the needle 102. In the storage position, the protective arm 60 cooperates with the protective cap 70 to prohibit access to the needle 102.

Figure 15B:
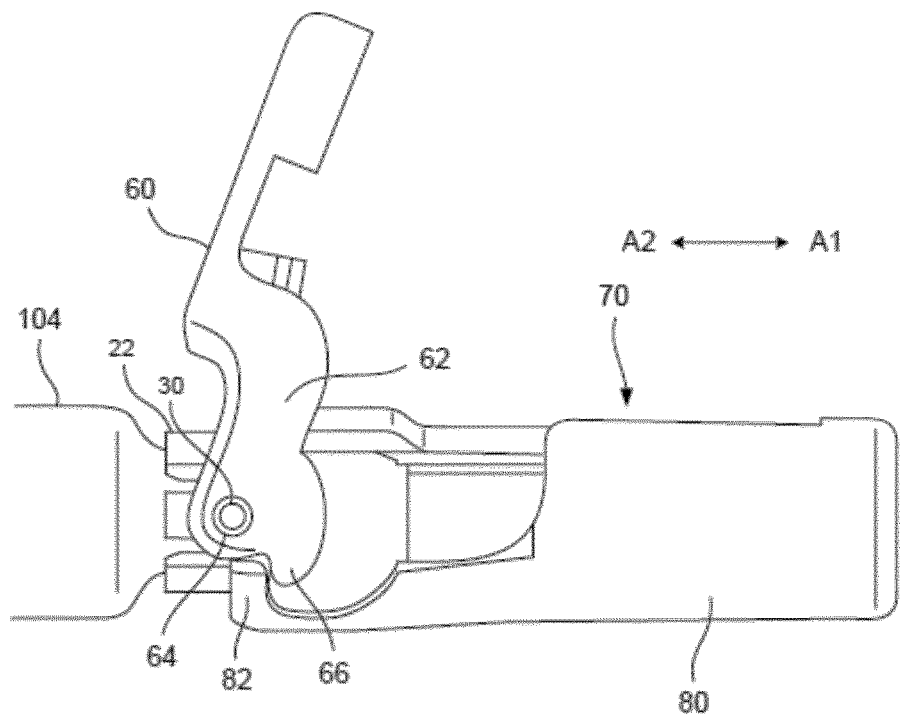

FIG. 15B shows the protective arm 60 in transition from the storage position to a retracted position. When the protective cap 70 is moved in the distal direction A1, the engaging peg 82 of protective cap 70 pushes the cam surface 66 of the protective arm 60. The interaction between the engaging peg 82 and the cam surface 66 results in a rotary movement of the protective arm 60 with respect to the outer ring 22.

Figure 15C:
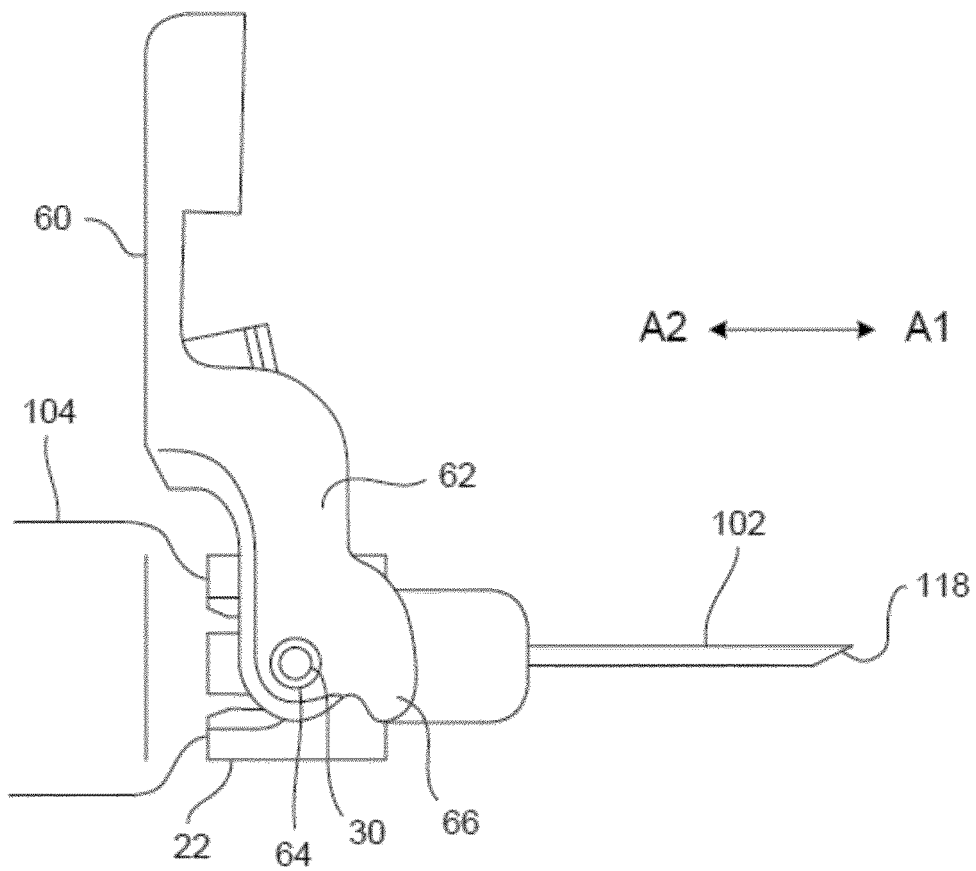

FIG. 15C shows the protective arm 60 in retracted position. In this position, the protective arm 60 is at right angle relative to the needle 102 and the protective cap 70 is completely removed from the needle 102. As can be seen from the drawing, the safety assembly 10 is now open to give full access to the needle 102. The medical device 1 is ready to use, for example to inject a medical product into the body of a patient.

Figure 15D:
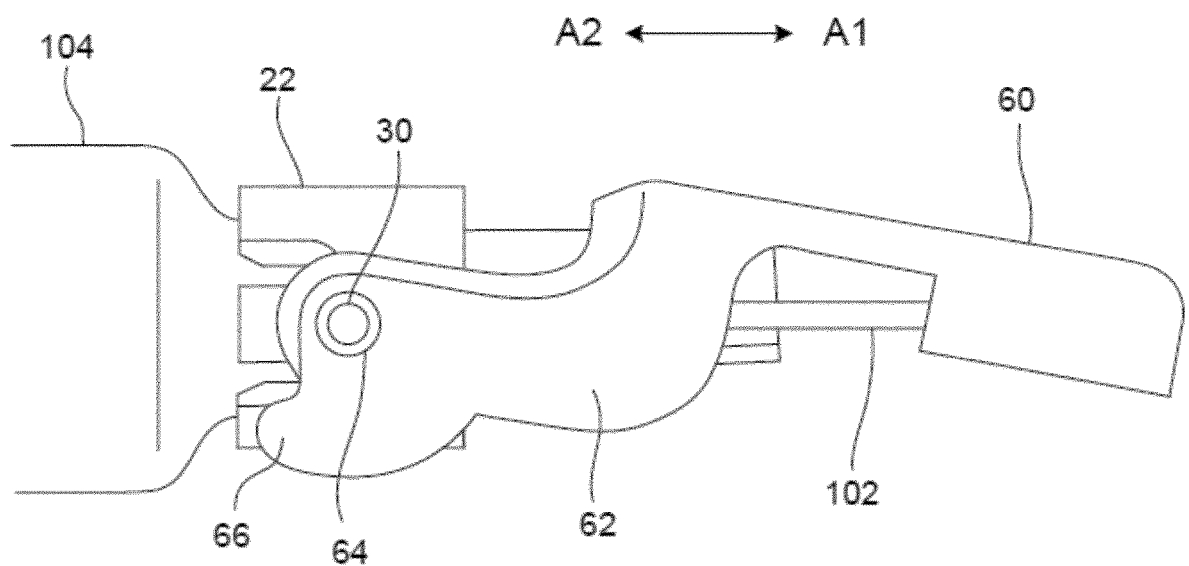

FIG. 15D shows the protective arm 60 in a safety position. Once the injection is performed, the user may apply a force to the protective arm 60 to rotate the protective arm 60 back in order to cover the needle 102 with the protective arm 60.

The protective cap 70 is illustrated by way of example and may also have other configurations. For example, the protective cap 70 may comprise only one shield, e.g. the rigid shield 80.

Besides, the invention is not limited to a safety device comprising a protective cap and a protective arm as illustrated in FIGS. 1 and 15A-15D, but to any safety device intended to be attached to the tip of the medical container. To that end, the safety device comprises a part configured to be attached to the outer ring 22. For sake of concision only and without any intended limitation, the following description is based on the safety device illustrated in FIGS. 1 and 15A-15D.

Figure 2A:
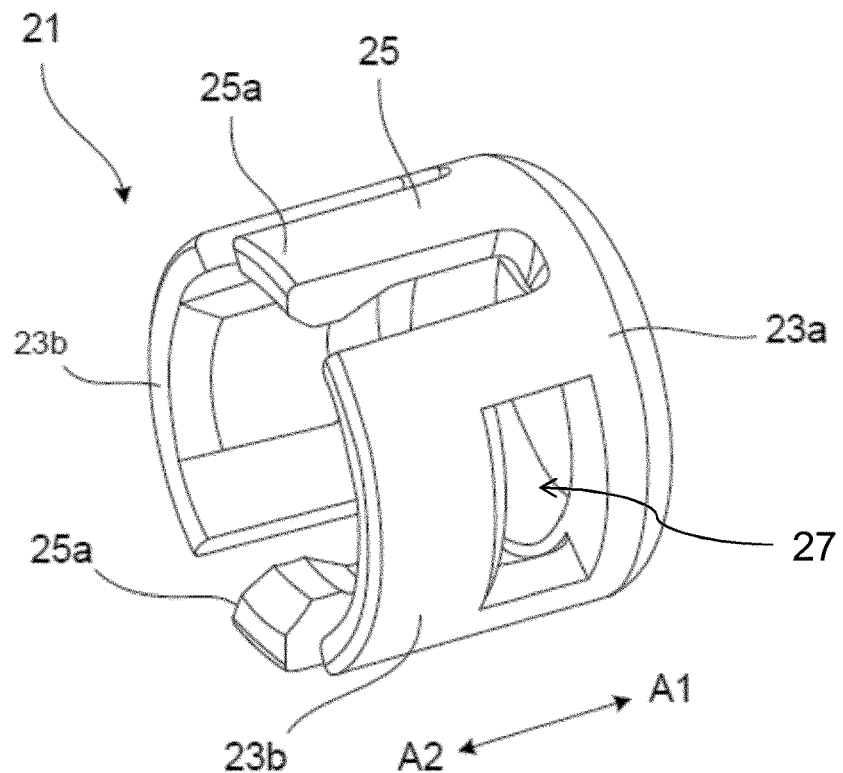
FIG. 2A is a perspective view illustrating an inner ring according to one example.
Figure 2B:
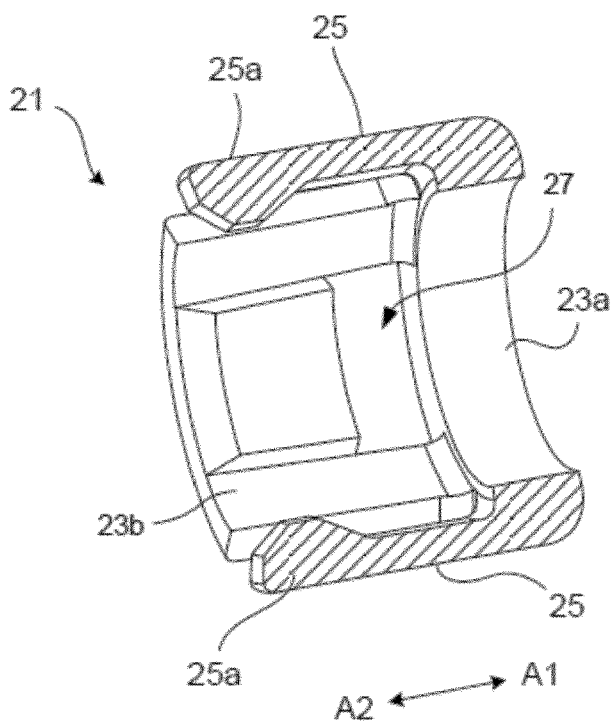
FIG. 2B shows a half portion of the inner ring of FIG. 2A which is cut on a plane extending along a central axis of the inner ring.

Referring to FIGS. 2A and 2B, the inner ring 21 will be described. The inner ring 21 is configured to be snapped on the tip of the medical container. To that purpose, the inner ring 21 comprises snap features configured to be snapped into the complementary snap features of the tip of the medical container. In this embodiment, the inner ring 21 comprises an annular distal ring 23a, and mounting fingers 25 extending proximally from the distal ring 23a. In this embodiment, the inner ring 21 is made in a single piece.

The distal ring 23a is dimensioned to receive the tip 106 of the container 100.

Each mounting finger 25 has a snap feature. In this embodiment, the snap feature comprises a groove 27 and an inwardly protruding protrusion 25a at its proximal end. In the illustrated example, two mounting fingers 25 are provided, but the inner ring 21 may have three or more mounting fingers.

The mounting fingers 25 are preferably diametrically opposed to each other around the central axis.

The inner ring 21 has a groove 27 formed on the inner circumference of the inner ring 21 around the central axis. The groove 27 runs on the inner face of the mounting fingers 25. A proximal end of the groove 27 is delimited by the inwardly protruding protrusions 25a of the mounting fingers 25. A distal end of the groove 27 could be directly delimited by the distal ring 23a or by a distal protrusion between the groove and the distal ring. The groove 27 is configured to receive the bump 110 on the tip 106.

The inner ring 21 is configured to be inserted on the tip 106 of the container 100 by axially moving the inner ring 21 towards the tip 106. During the axial movement of the inner ring 21 towards the tip 106, the inwardly protruding protrusions 25 move radially outwardly and the mounting fingers 25 are flexed outwardly, so that the inwardly protruding protrusions 25a can move beyond the bump 110. When the inwardly protruding protrusions 25a are proximally from the bump 110, the inner ring is securely attached to the container's tip. The inwardly protruding protrusions 25a are maintained proximally from the bump 110 thanks to the outer ring as explained thereafter.

Figure 3A:
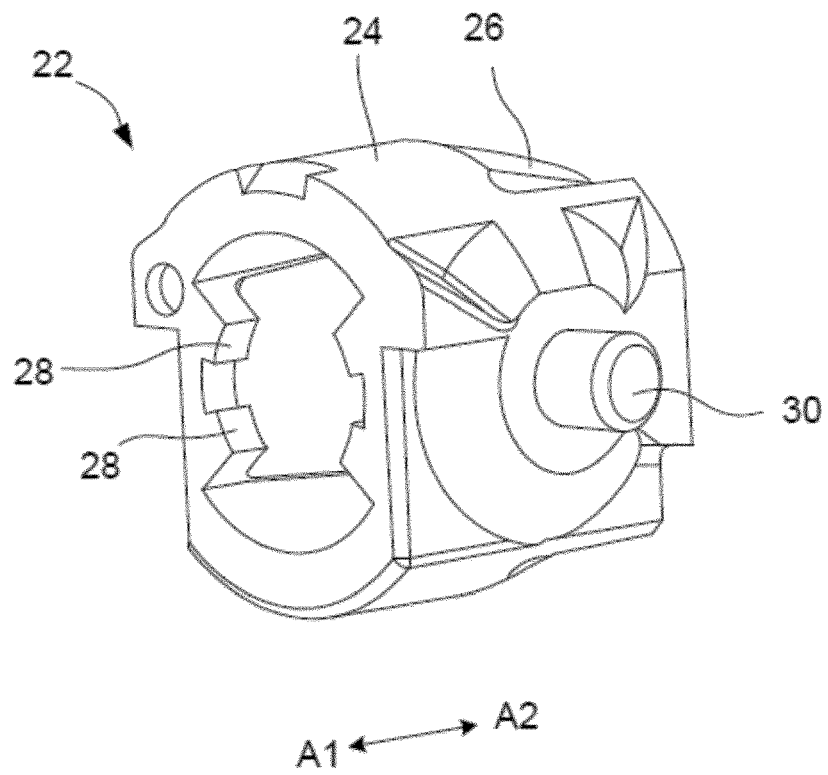
FIG. 3A is a perspective view illustrating an outer ring according to one example.
Figure 3B:
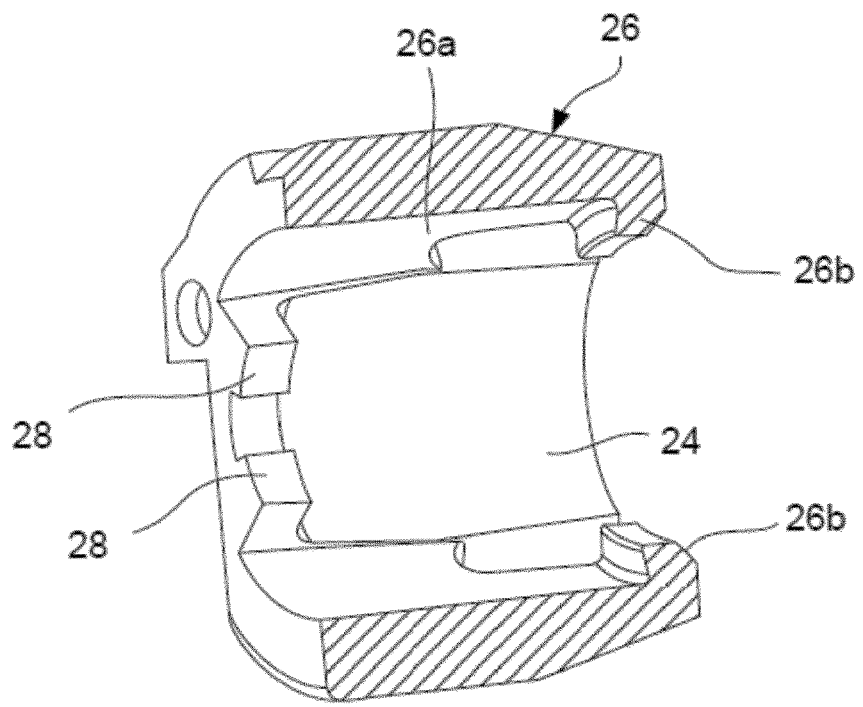
FIG. 3B shows a half portion of the outer ring of FIG. 3A which is cut on a plane extending along a central axis of the inner ring.

Referring to FIGS. 3A and 3B, the outer ring 22 will be described. The outer ring 22 is configured to be clipped on the inner ring 21. The outer ring 22 has a sleeve portion 24 surrounding at least one part of the inner ring in order to prevent radial movement of the snap feature, thereby enabling to maintain the snap feature engaged with the complementary snap feature.

More precisely, in this embodiment, the sleeve portion 24 is configured to surround the mounting fingers 25 of the inner ring 21. The sleeve portion 24 defines an inner circumference around the central axis. The sleeve portion 24 receives at least part of the mounting fingers 25 of the inner ring 21, thereby preventing radial movement of the inwardly protruding protrusions 25a, as well as radial deformation of the mounting fingers 25.

The outer ring further comprises clipping features enabling to snap the outer ring on the inner ring. In this embodiment, the clipping features comprise locking fingers 26. The locking fingers 26 are configured to clip on the inner ring 21, thereby interlocking the inner ring 21 and the outer ring 22. Each locking finger 26 has a distal end 26a connected to the sleeve portion 24 and a proximal end 26b which protrudes radially inwardly. The proximal end 26b of the locking finger 26 is configured to be engaged with a flange 29 of the inner ring 21 which extends radially outwardly from the circumference of the inner ring 21, thereby interlocking the inner ring 21 and the outer ring 22.

The outer ring 22 may also have inner protrusions 28. The inner protrusions 28 extend radially inwardly. The inner protrusions 28 are preferably provided at the distal end of the outer ring 22. The inner protrusions 28 may have curved inner faces. The inner protrusions 28 are configured to frictionally engage the tip 106 of the container 100. Accordingly, the inner protrusions 28 are in contact with the outer circumferential face of the tip 106 when the outer ring 22 is fixed on the inner ring 21. The inner protrusions 28 prevent rotation between the safety assembly and the medical container.

The attachment ring 20 is used to attach the protective arm 60 and the protective cap 70 to the container 100.

Now turning to FIGS. 4A and 4B, process of assembling the attachment ring 20 with the medical container 100 will be described.

Figure 4A:
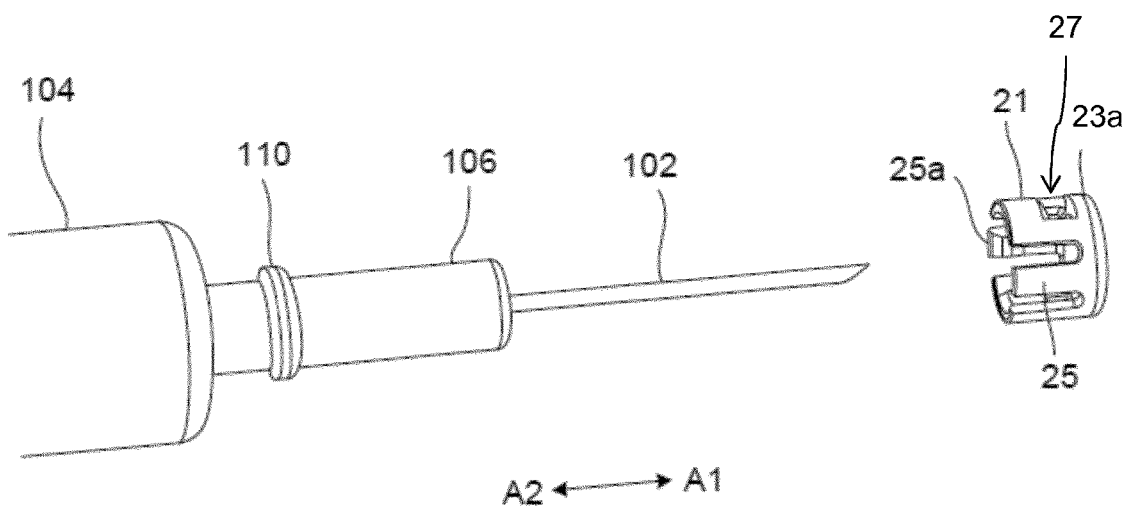
FIGS. 4A and 4B show the process of assembling an attachment ring with the medical container.

First, the inner ring 21 is brought in axial alignment with tip 106 and moved towards the container 100 in the proximal direction A2 (FIG. 4A). When the inner ring 21 reaches the bump 110 of the tip 106, the inwardly protruding protrusions 25a of the mounting fingers 25 come in contact with the bump 110 on the tip 106. As the inwardly protruding protrusions 25a move beyond the bump 110, the mounting fingers 25 elastically deform radially outwardly by the bump 110 on the tip 106. When the inner ring 21 advances farther in the proximal direction A2, the mounting fingers 25 return to their original shape and as a result the bump 110 is accommodated within the groove 27 of the inner ring 21. Thanks to the engagement between the bump 110 and the groove 27 of the inner ring 21, axial movement of the inner ring 21 relative to the container 100 can be prevented.

Figure 4B:
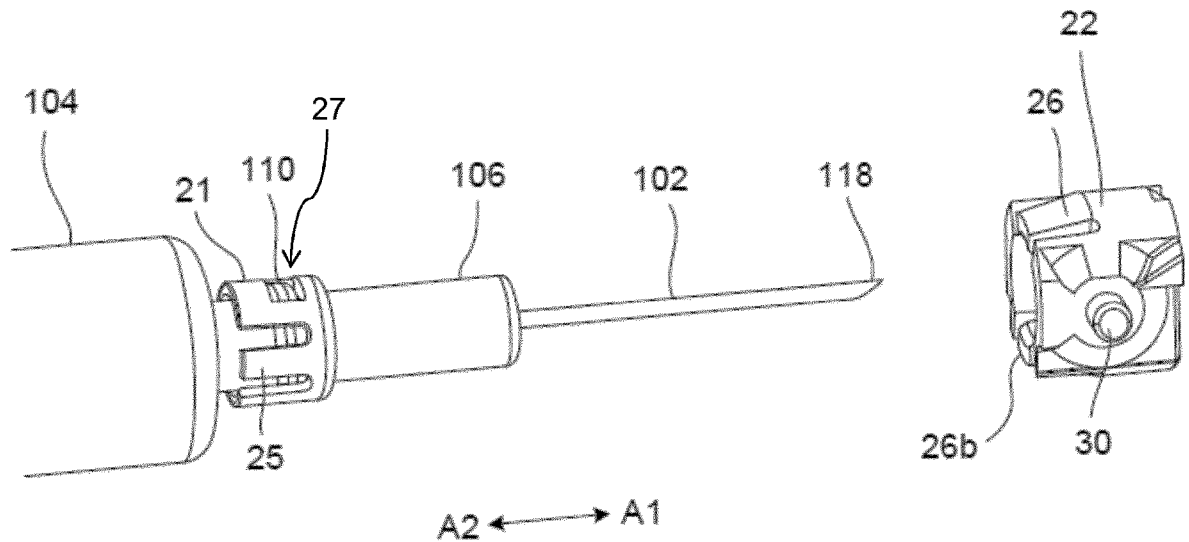

Then, the outer ring 22 is introduced onto the tip 106 in the proximal direction A2 (FIG. 4B). As the outer ring 22 is brought into contact with the inner ring 21, the locking fingers 26 of the outer ring 22 deform radially outwardly since the proximal ends 26a of the locking fingers 26 protrude radially inwardly. Once the proximal ends 26a of the locking fingers 26 move beyond the inner ring 21, the locking fingers 26 return to their original shapes, which establishes engagement between the locking fingers 26 and the inner ring 21 (FIG. 5).

As shown in FIG. 5, when the attachment ring 20 is assembled with and in position relative to the container 100, the bump 110 of the container 100 is received within the groove 27 of the inner ring 21. In addition, the locking fingers 26 of the outer ring 22 are engaged with a flange 29 of the inner ring 21 which extends from the proximal end of the inner ring 21. This configuration can advantageously prevent axial movement of the inner ring 21 relative to the container 100, as well as axial movement of the outer ring 22 relative to the inner ring 21. In the illustrated embodiment, the flange 29 corresponds to the proximal end of the mounting fingers 25.

According to this example, pull-out force which would be required to pull the attachment ring 20 from the container tip 106 is increased. In particular, the sleeve portion 24 of the outer ring 22 surrounds the mounting fingers 25 of the inner ring 21 and prevents the mounting fingers 25 from deforming radially outwardly. Since the radial deformation of the mounting fingers 25 would be required to disengage the inner ring 21 from the bump 110 of the container, it is ensured that the interlock between the attachment ring 20 and the container tip 106 is maintained.

The sleeve portion 24 of the outer ring 22 can prevent any radial movement of the inwardly protruding protrusions 25a of the mounting fingers 25, thereby preventing the inner ring 21 from being removed from the container 100.

Figure 6:
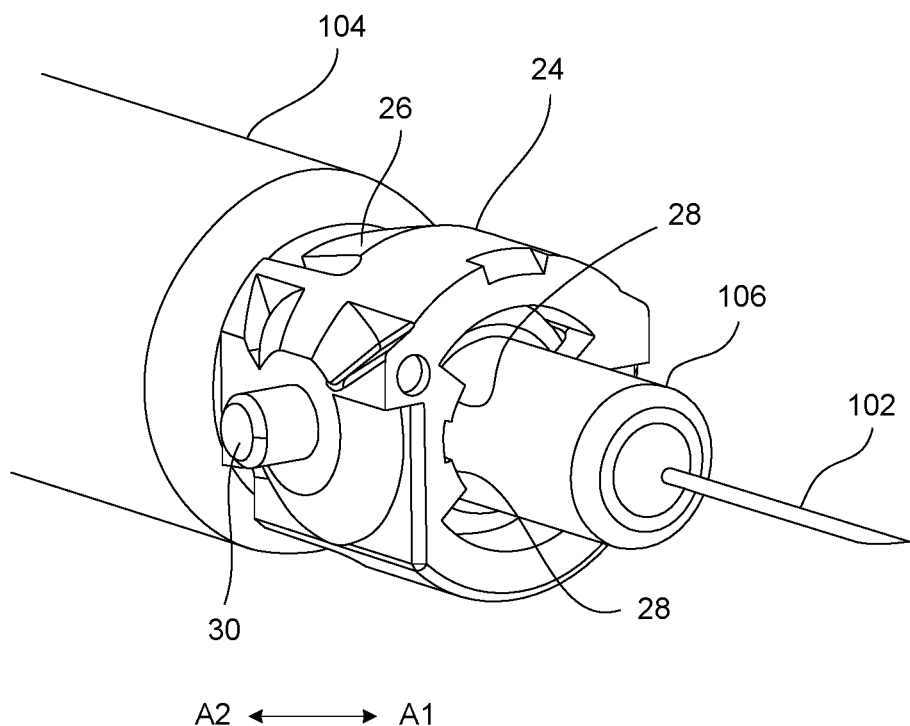
FIG. 6 is a perspective view illustrating the attachment ring attached to the tip of the medical container.

As shown in FIG. 6, the inner protrusions 28 are frictionally engaged with the outer surface of the container tip 106. Thanks to the friction generated between the inner protrusions 28 and the tip 106, a rotational torque that may be applied to the outer ring 22 is prevented from being transmitted to the inner ring 21. This is also advantageous to ensure that the attachment ring 20 is reliably attached to the container 100.

Figure 7A:
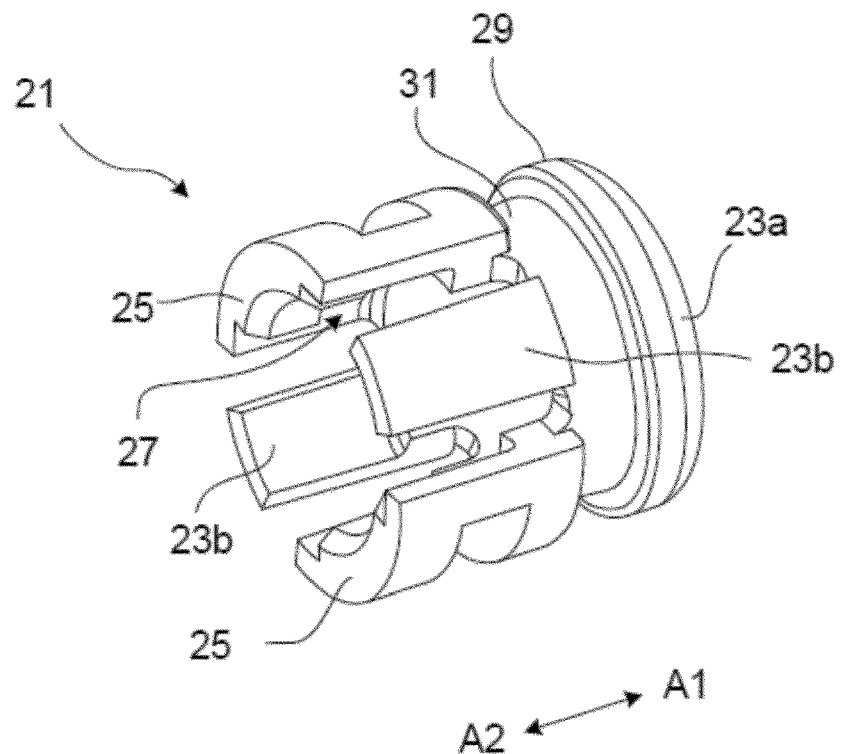
FIG. 7A is a perspective view illustrating an inner ring according to another example.
Figure 7B:
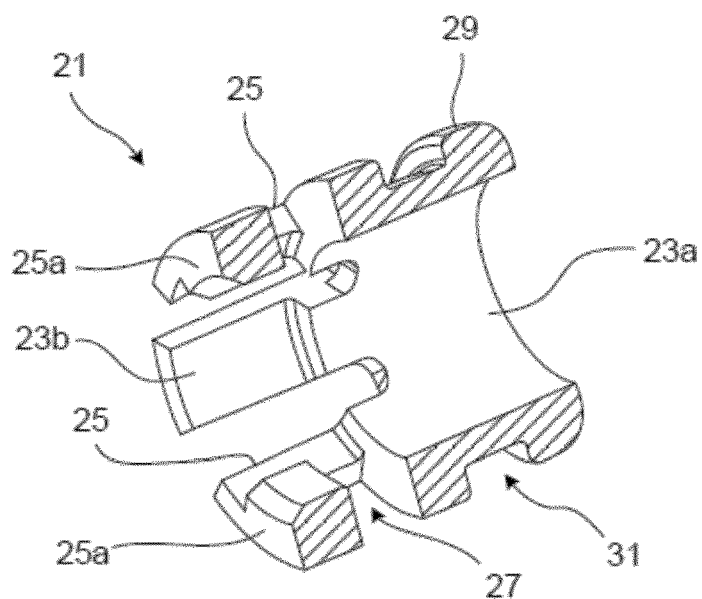
FIG. 7B shows a half portion of the inner ring of FIG. 7A which is cut on a plane extending along a central axis of the inner ring.

FIGS. 7A and 7B show another example of the attachment ring 20. According to this example, the inner ring 21 further has an outer groove 31. The outer groove 31 is on an external face of the inner ring 21. The outer groove 31 is arranged between the distal ring 23a and the proximal end of the mounting fingers 25. The outer groove 31 is an annular groove intended to receive the locking fingers 26 of the outer ring 22.

Figure 8A:
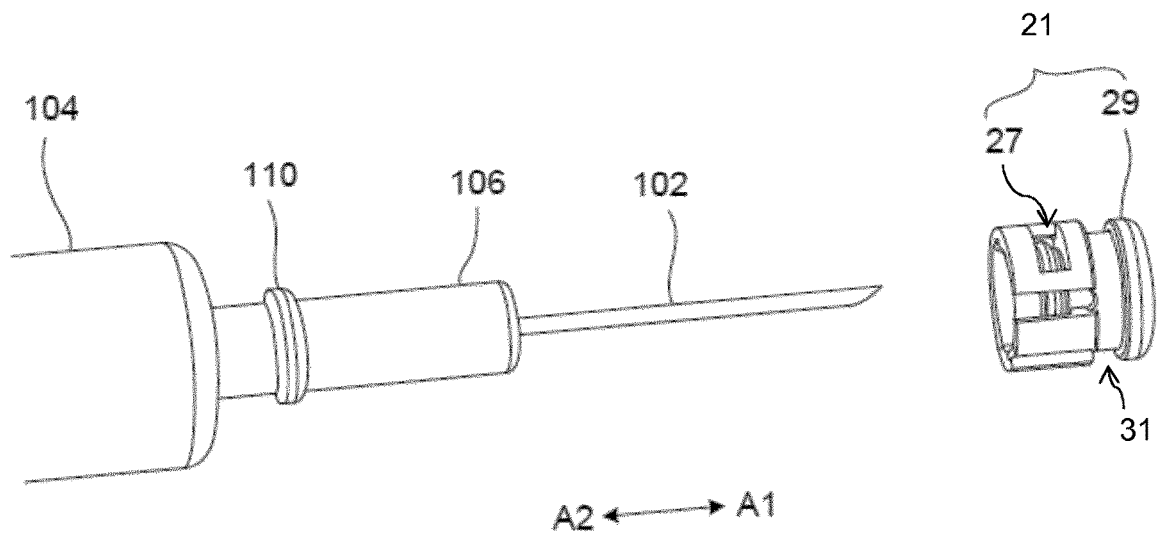
FIGS. 8A and 8B show the process of assembling an attachment ring with the medical container.
Figure 9A:
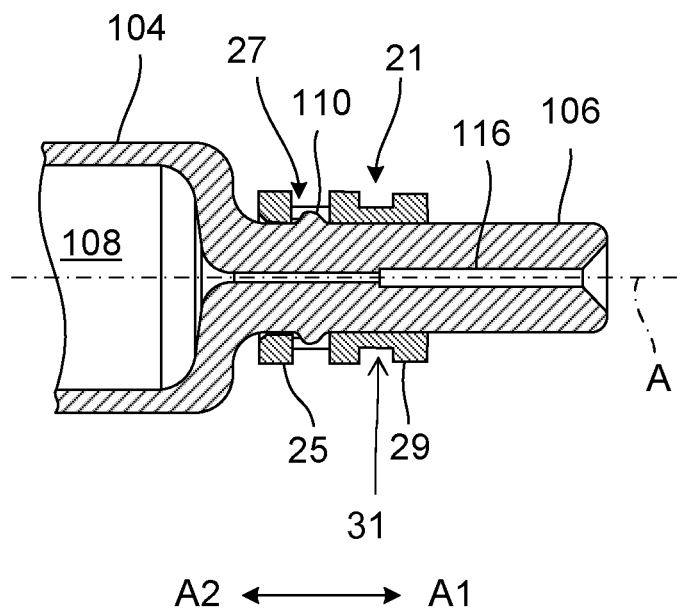
FIG. 9A is a longitudinal sectional view illustrating the tip of the container provided with the inner ring of FIG. 7A.

The inner ring 21 can be snap-fit to the container tip 106 in the same way as the inner ring 21 shown in FIGS. 2A and 2B. The inner ring 21 is introduced onto the tip 106 in the proximal direction A2 (see FIG. 8A). As the inner ring 21 comes in contact with the bump 110 on the tip, the inwardly protruding protrusions 25a of the mounting fingers 25 are raised by the bump 110, the mounting fingers 25 deform radially outwardly. Then, the inner ring 21 further advances in the proximal direction A2 until the inwardly protruding protrusions 25a move beyond the bump 110 and the bump 110 is accommodated within the groove 27 of the inner ring 21 (FIG. 9A).

Figure 8B:
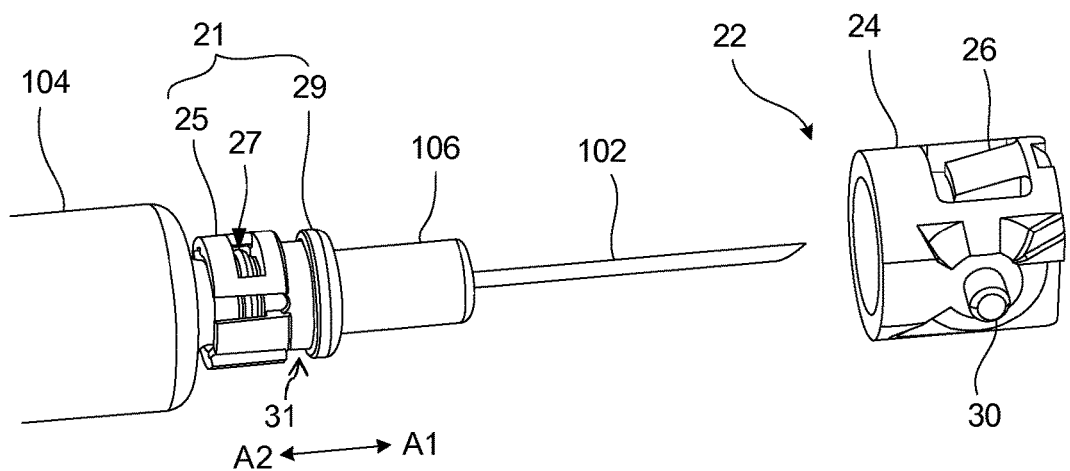
Figure 9B:
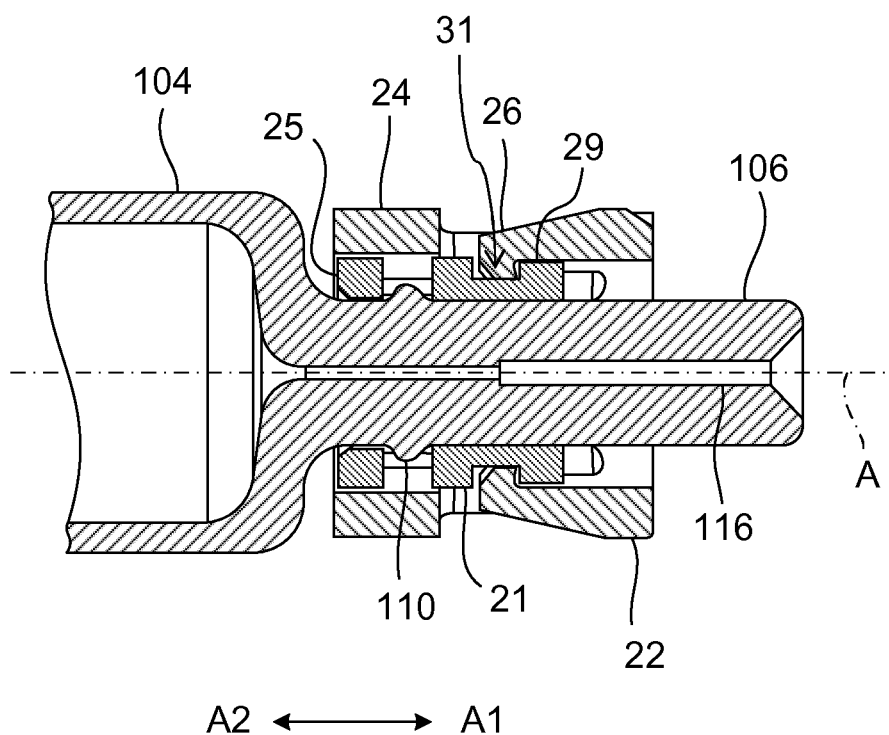
FIG. 9B is a longitudinal sectional view illustrating the tip of the container provided with the attachment ring.

Thereafter, as shown in FIG. 8B, the outer ring 22 is introduced onto the inner ring 21. The outer ring 22 has locking fingers 26 in a corresponding position to the outer groove 31 such that the sleeve portion 24 surrounds the mounting fingers 25 of the inner ring 21, and at the same time the locking fingers 26 engage with the outer groove 31. The engagement between the inner ring 21 and the outer ring 22 is illustrated in FIG. 9B.

Figure 10:
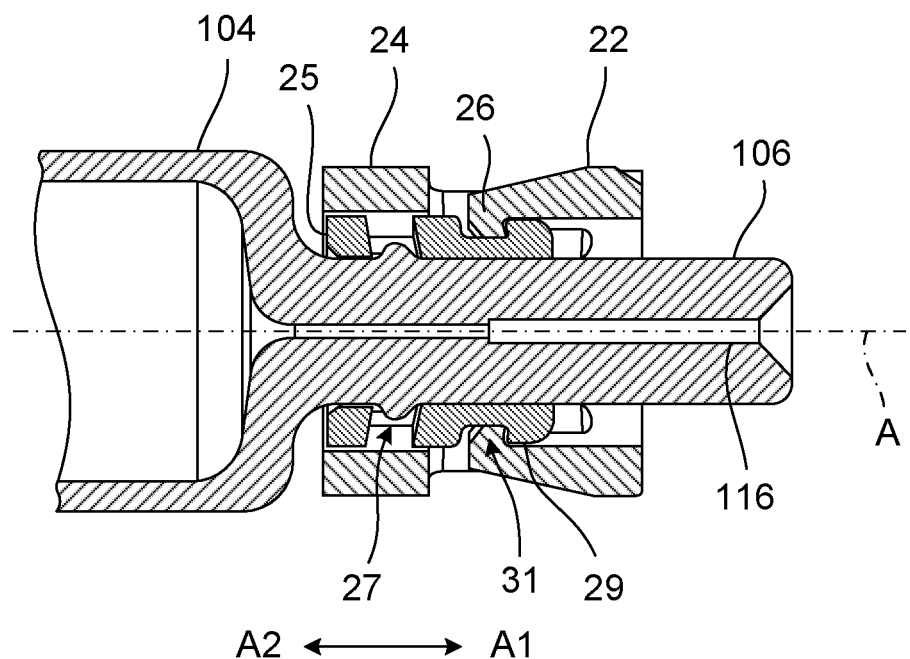
FIG. 10 shows the tip of the container in a similar manner to FIG. 9B, but according to another example in which the inner ring has inclined walls.

According to another example shown in FIG. 10, the end walls (proximal and distal end faces) of the outer groove 31 of the inner ring 21 for receiving the locking fingers 26 are inclined relative to a plane perpendicular to the central axis of the inner ring 21. The inclination angle may be of 10 degrees. However, the inclination angle may also range between 3 degrees and 45 degrees, preferably between 5 and 15 degrees. The inclined walls of the outer groove enable to have a better attachment between the tip of the container and the inner ring.

The end walls of the groove 27 of the inner ring 21 which are configured to receive the bump 110 of the container tip 106 may also be inclined. The inclination angle may be at 10 degrees. However, the inclination angle may also range between 3 degrees and 45 degrees, preferably between 5 and 15 degrees. Thanks to the inclined end walls of the grooves 27, the interlock between the outer ring 22 and the inner ring 21 is more reliable.

Referring to FIGS. 11A to 13, a safety assembly according to yet another example will be described. In this example, the inner ring 21 comprises two half rings 21A and 21B. The inner ring 21 is separable by moving the half rings 21A and 21B radially outwardly.

Figure 11A:
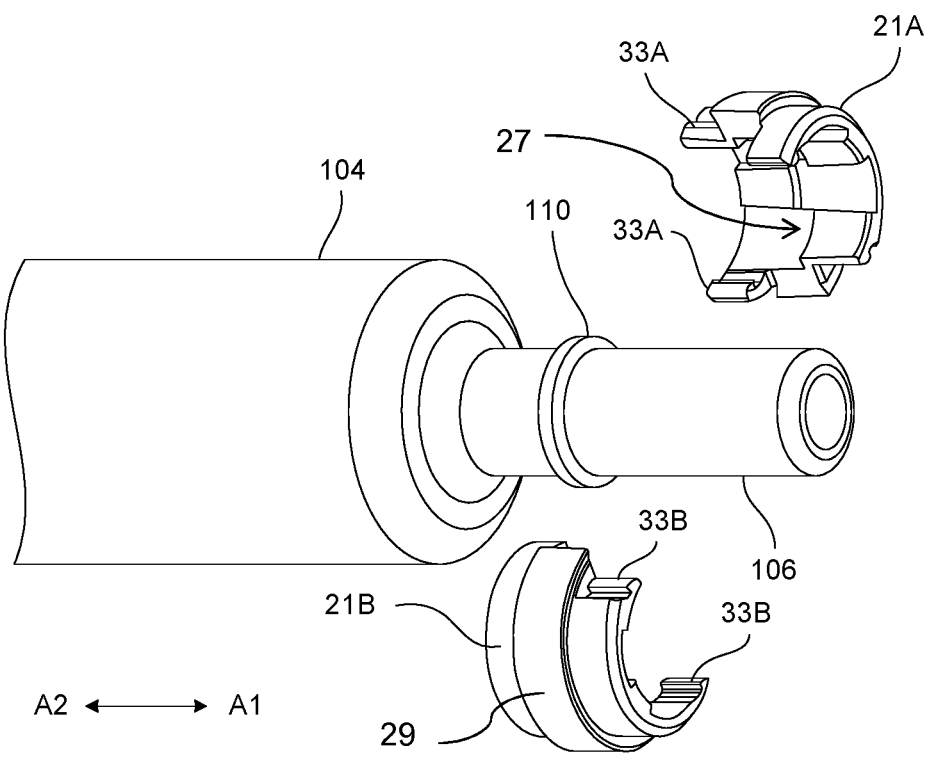
FIGS. 11A to 11C show the process of assembling an attachment ring with the medical container.
Figure 12:
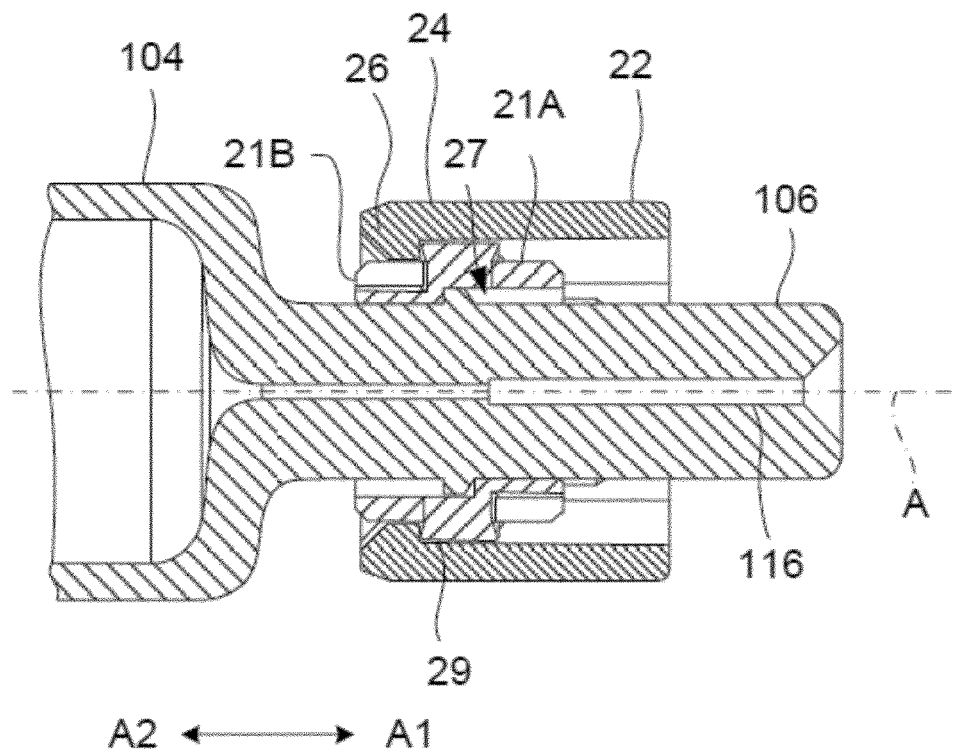
FIG. 12 is a longitudinal sectional view illustrating the tip of the container provided with the attachment ring.
Figure 13:
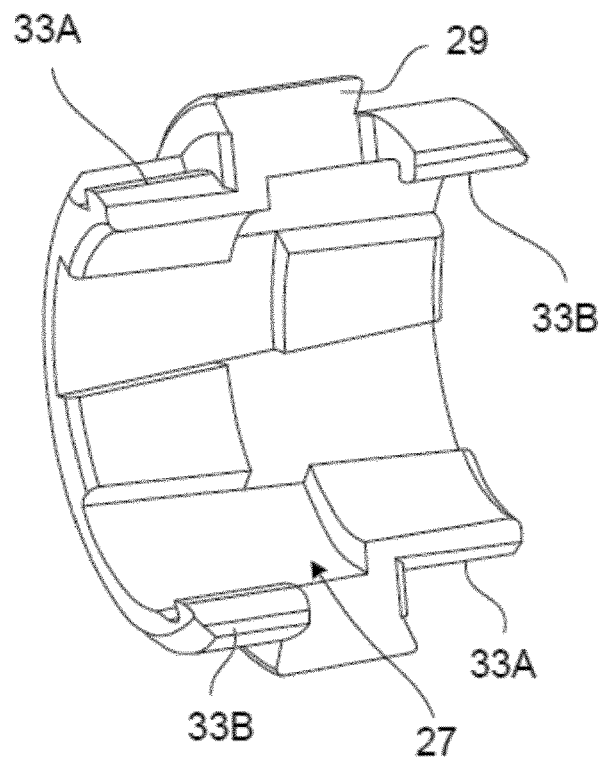
FIG. 13 is a perspective view illustrating a half ring of the inner ring.

As shown in FIGS. 11A, 12 and 13, each half ring 21A and 21B has an inner face provided with a snap feature configured to engage the complementary snap feature of the tip of the container. In this example, the snap feature comprises a groove 27 configured to be clipped on the bump 110 of the container's tip 106. However, the snap feature could also be a lip configured to be inserted in a groove of the tip of the container.

As previously described, the outer ring 22 is clipped on the inner ring such that the sleeve portion 24 surrounds the two half rings 21A and 21B when assembled together, thereby preventing radial movement of the two half rings 21A and 22B. Since the two half rings 21A and 21B cannot move radially, the snap feature is maintained engaged with the complementary snap feature such that the attachment ring cannot move axially.

The half rings 21A and 21B may have a flange 29 onto which the locking fingers 26 of the outer ring 22 can be snapped (see FIG. 12). In this example, the flange 29 may be formed on an outer face of the inner ring 21.

The flange 29 has a proximal wall that is inclined relative to a plane which extends perpendicular to a central axis of the inner ring, so as to increase the pull-out force required to pull the locking fingers 26 of the outer ring from the flange 29. This ensures that the attachment ring cannot be removed easily by accident.

Although this inclination of the flange is illustrated on FIGS. 12 and 13, it could be applied also to the other embodiments described in the present text.

The half rings 21A and 21B may be identical. The half rings 21A and 21B may also be each provided with hook portions 33A and 33B at opposite ends in the circumferential direction. The hook portions 33A and 33B have complementary shapes to each other such that the half rings 21A and 21B can be interlocked with each other.

Figure 11B:
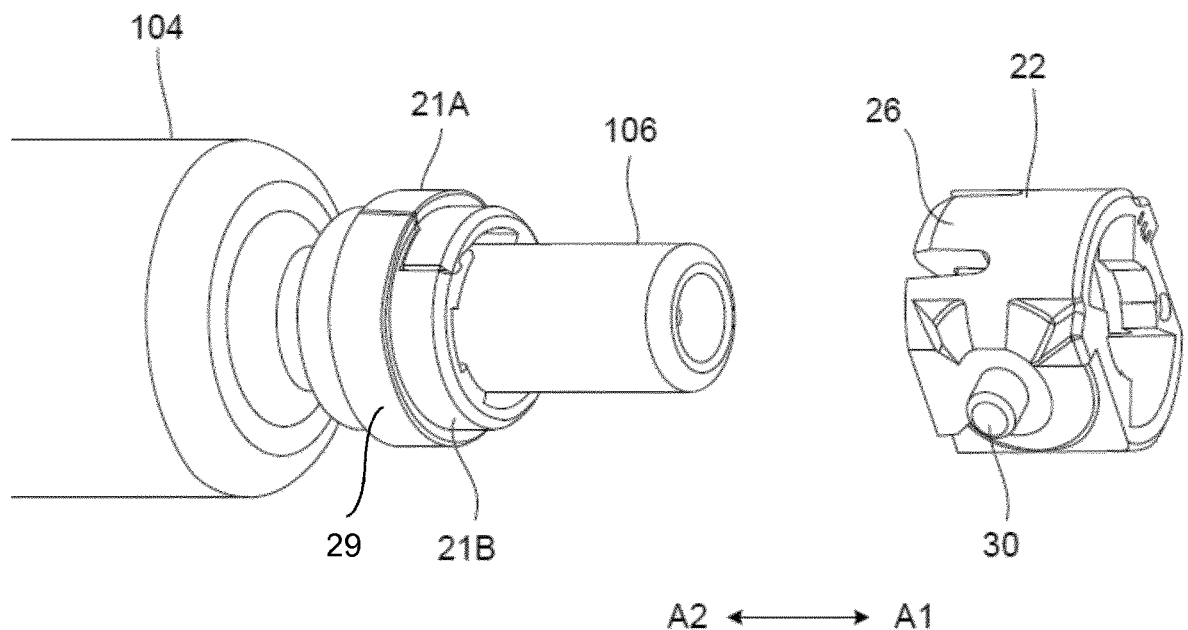
Figure 11C:
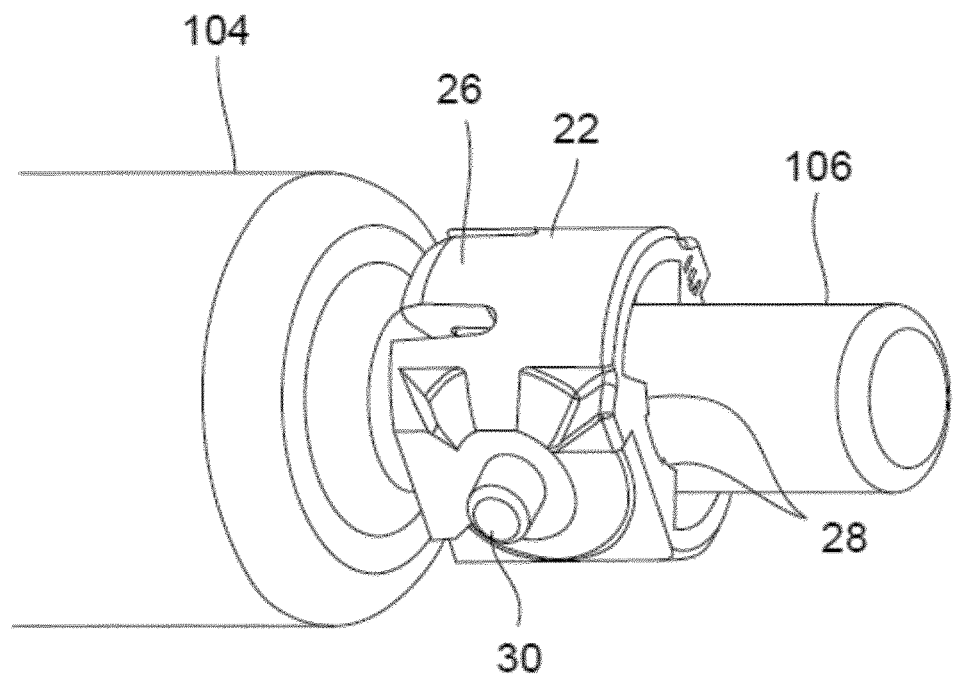

As shown in FIGS. 11A and 11B, the inner ring 21 can be assembled by bringing the two half rings 21A and 21B closer to each other in the radially inwardly and interlock them by way of the hook portions 33A and 33B. When the inner ring 21 is attached to the container tip 106 (FIG. 11B), the bump 110 of the tip 106 is accommodated within the groove 27 of the inner ring 21.

The outer ring 22 can then be snap-fit with the inner ring 21 by introducing the outer ring 22 in the proximal direction A2 (see FIGS. 11B and 11C) so that the sleeve portion 24 of the outer ring 22 surrounds the two half rings 21A and 21B. As can be seen from FIG. 12, the sleeve portion 24 of the outer ring 22 extends over the half rings 21A and 21B, thereby holding them together, preventing them from moving radially outwardly to disengage the hook portions 33A and 33B.

According to this example, the radial movement of the two half rings 21A and 21B, which is required to detach the inner ring 21 from the container tip 106, can be prevented by the sleeve portion 24 of the outer ring 22. In addition, the outer ring 22 is clipped on the inner ring 21. Therefore, the connection between the attachment ring 20 and the container becomes more reliable.

Further, the inner ring 21 can be easily attached to the tip 106 of the container, simply by bringing the two half rings 21A and 21B closer to each other and engaging the corresponding hook portions 33A and 33B. The assembling process of the inner ring 21 is simplified, and the manufacturing cost of the safety assembly 10 can be reduced.

When the half rings 21A and 21B are identical, the manufacturing cost of the safety assembly 10 can be reduced.

Figure 14:
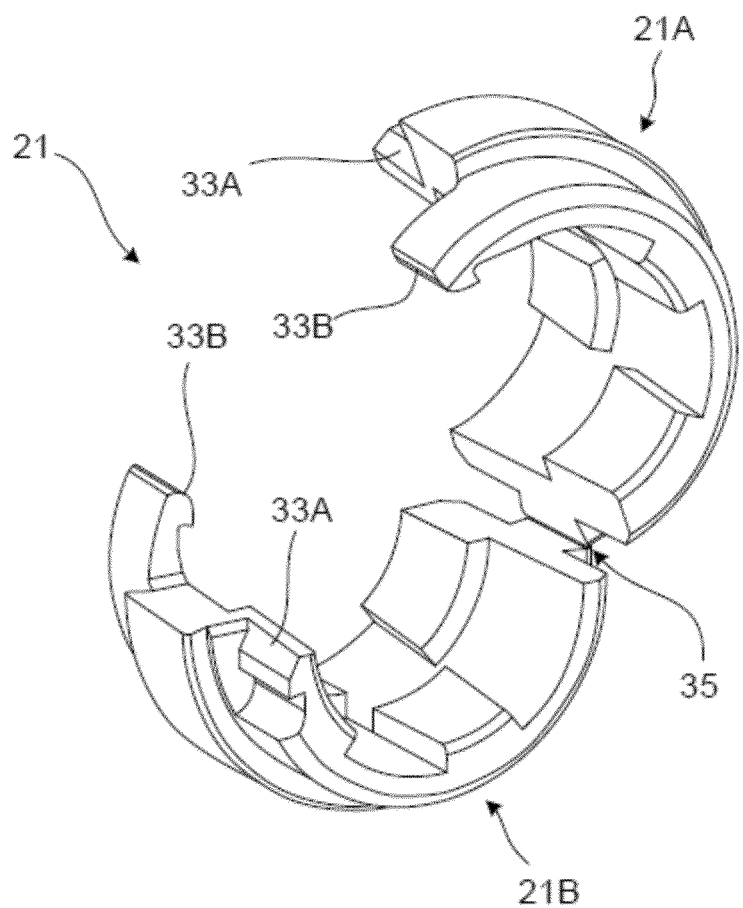
FIG. 14 is a perspective view illustrating an inner ring according to another example.

FIG. 14 shows another example of the half rings 21A and 21B. According to this embodiment, the half rings 21A and 21B are integrally formed with each other and connected via a hinge 35. The half rings 21A and 21B can be assembled with or disassembled from each other by pivot movement of the half rings 21A and 21B about the hinge 35. This can facilitate process of assembling the two half rings 21A and 21B to form the inner ring 21.

The safety assembly 10 may also be used with any medical container equipped with a needle which poses a potential risk of needle stick injury, including but not being limited to pen-injectors, catheters, blood collection devices. The medical device 1 may be used for delivering a pharmaceutical composition, vitamins, a vaccine or any other type of medical solution to the body of a patient or for taking samples from the body of a patient.

Of course, the invention is not limited to the embodiments described with reference to the drawings and some alternatives could be envisaged without departing the scope of the invention. For example, the clipping means between the outer ring and the inner ring of FIGS. 5 to 10 could be used in any embodiments of FIGS. 11A to 14. Besides, we could use as snap feature a lip instead of a groove in any embodiment.

The invention claimed is:

1. A safety assembly for preventing needle stick injury with a needle, the needle having a proximal end fixed to a tip of a medical container and a pointed distal end, the safety assembly comprising:
   an attachment ring configured to be attached to the tip of the medical container; and
   a safety device configured to cover at least the distal end of the needle, the safety device being attached to the attachment ring,
   wherein the attachment ring comprises:
   an inner ring having an inner face provided with a snap feature, the snap feature being configured to engage a complementary snap feature on the tip of the medical container in order to prevent axial movement of the inner ring with respect to the medical container, the snap feature being configured to move radially to engage the complementary snap feature on the tip of the container,
   an outer ring fixed on the inner ring, the outer ring comprising a sleeve portion configured to surround at least a portion of the inner ring in order to prevent radial movement of the snap feature once the snap feature has engaged the complementary snap feature on the tip of the medical container, and wherein the outer ring has an inner protrusion extending radially inwardly and being configured to frictionally engage the tip of the medical container.

2. The safety assembly of claim 1, wherein the inner ring comprises a distal ring and an at least one mounting finger extending proximally from the distal ring, the snap feature being formed at a proximal end of said at least one mounting finger, the at least one mounting finger being able to be deformed radially outwardly, the outer ring being fixed on the inner ring such that the sleeve portion surrounds the at least one mounting finger to prevent radial deformation of the at least one mounting finger.

3. The safety assembly of claim 1, wherein the inner ring comprises two half rings each having an inner face provided with a portion of the snap feature, the two half rings being configured to be interlocked around the tip of the container such that the snap feature engages the complementary snap feature on the tip of the container in order to prevent axial movement of the inner ring with respect to the container, the sleeve portion of the outer ring being configured to surround the two half rings to prevent radial movement of the two half rings.

4. The safety assembly of claim 1, wherein the outer ring comprises a clipping feature clipped into a complementary clipping feature of the inner ring.

5. The safety assembly of claim 1, wherein the inner ring has a flange extending radially outwardly, and the outer ring has at least one locking finger extending proximally and having a proximal end extending radially inwardly, the proximal end of the at least one locking finger being engaged with the flange of the inner ring to interlock the outer ring with the inner ring.

6. The safety assembly of claim 5, wherein the flange extends from a proximal end of the inner ring.

7. The safety assembly of claim 5, wherein the flange is arranged on a circumferential outer face of the inner ring.

8. The safety assembly of claim 5, wherein the flange of the inner ring comprises a proximal wall inclined relative to a plane which extends perpendicular to a central axis of the inner ring.

9. The safety assembly of claim 1, wherein the safety device further comprises:
a protective cap configured to cover the needle and inserted on the attachment ring and
a protective arm attached to the attachment ring such that the protective arm is pivotally movable between a storage position in which the protective arm is interlocked with the protective cap,
a retracted position in which the protective arm releases the protective cap to give access to the needle, and
a safety position in which the protective arm covers the needle.

10. The safety assembly of claim 9, wherein the protective cap is configured to be removed from the tip of the medical container by axial movement in a distal direction.

11. The safety assembly of claim 9, wherein the protective arm comprises a proximal extremity provided with a cam surface, and the protective cap comprises a proximal extremity provided with an engaging peg, the cam surface and the engaging peg being arranged so that, when the safety assembly is mounted around the tip of the medical container, removing the protective cap from the tip by a distal movement displaces the protective arm from the storage position to the retracted position.

12. A medical device comprising:
a medical container having a barrel, the tip extending from the barrel in a distal direction, and the complementary snap feature on the tip;
the needle attached to the tip of the medical container; and
a safety assembly according to claim 1,
the safety assembly being attached to the tip of the medical container such that the snap feature of the inner ring is engaged with the complementary snap feature of the medical container.

13. The medical device of claim 12, wherein the complementary snap feature is a bump, the snap feature comprising a groove delimited proximally by an inwardly protruding protrusion configured to be inserted proximally from the bump.

14. The medical device of claim 12, wherein the complementary snap feature is a groove, the snap feature comprising an inwardly protruding protrusion configured to be inserted into the groove.

15. A safety assembly for preventing needle stick injury with a needle, the needle having a proximal end fixed to a tip of a medical container and a pointed distal end, the safety assembly comprising:
an attachment ring configured to be attached to the tip of the medical container;
a safety device configured to cover at least the distal end of the needle, the safety device being attached to the attachment ring;
wherein the attachment ring comprises:
an inner ring having an inner face provided with a snap feature, the snap feature being configured to engage a complementary snap feature on the tip of the medical container in order to prevent axial movement of the inner ring with respect to the medical container, the snap feature being configured to move radially to engage the complementary snap feature on the tip of the container,
an outer ring fixed on the inner ring, the outer ring comprising a sleeve portion configured to surround at least a portion of the inner ring in order to prevent radial movement of the snap feature once the snap feature has engaged the complementary snap feature on the tip of the medical container, and
wherein the inner ring comprises two half rings each having an inner face provided with at least a snap feature, the two half rings being configured to be interlocked around the tip of the container such that the snap features engage complementary snap features on the tip of the container in order to prevent axial movement of the inner ring with respect to the container, the sleeve portion of the outer ring being configured to surround the two half rings to prevent radial movement of the two half rings.

16. A medical device comprising:
a medical container having a barrel, the tip extending from the barrel in a distal direction, and the complementary snap feature on the tip;
the needle attached to the tip of the medical container; and
a safety assembly according to claim 15,
the safety assembly being attached to the tip of the medical container such that the snap feature of the inner ring is engaged with the complementary snap feature of the medical container.

* * * * *